United States Patent
Sellers et al.

(10) Patent No.: US 11,524,097 B2
(45) Date of Patent: Dec. 13, 2022

(54) MEDICAL DEVICE WITH HYDROPHILIC COATING

(71) Applicant: Hollister Incorporated, Libertyville, IL (US)

(72) Inventors: Brent H. Sellers, Libertyville, IL (US); Horacio Montes De Oca, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 17/064,722

(22) Filed: Oct. 7, 2020

(65) Prior Publication Data

US 2021/0015979 A1 Jan. 21, 2021

Related U.S. Application Data

(63) Continuation of application No. 16/077,129, filed as application No. PCT/US2017/018073 on Feb. 16, 2017, now Pat. No. 10,850,009.

(60) Provisional application No. 62/298,728, filed on Feb. 23, 2016.

(51) Int. Cl.
| | | |
|---|---|---|
| *A61M 25/00* | (2006.01) | |
| *A61L 29/08* | (2006.01) | |
| *A61L 29/04* | (2006.01) | |
| *A61L 29/14* | (2006.01) | |
| *A61L 29/06* | (2006.01) | |

(52) U.S. Cl.
CPC .......... *A61L 29/085* (2013.01); *A61L 29/041* (2013.01); *A61L 29/049* (2013.01); *A61L 29/06* (2013.01); *A61L 29/14* (2013.01); *A61M 25/0045* (2013.01); *A61L 2400/10* (2013.01); *A61L 2430/22* (2013.01); *A61M 2025/0046* (2013.01)

(58) Field of Classification Search
CPC ...... A61L 29/085; A61L 29/041; A61L 29/06; A61L 29/14; A61L 2400/10; A61L 2430/10; A61L 27/34; A61M 25/0045; A61M 2025/0046; Y10T 428/31536; C10M 157/00; C10M 157/04
USPC ............ 604/544, 265; 427/2.1; 525/178, 56
See application file for complete search history.

(56) References Cited

U.S. PATENT DOCUMENTS

| | | |
|---|---|---|
| 5,225,120 A | 7/1993 | Gravier |
| 5,331,027 A | 7/1994 | Whitbourne |
| 5,731,087 A | 3/1998 | Fan |
| 6,221,425 B1 | 4/2001 | Michal |
| 8,377,498 B2 | 2/2013 | Rindlav-Westling |
| 8,888,759 B2 | 11/2014 | Schmid |
| 2003/0094736 A1 | 5/2003 | Qin |
| 2007/0016169 A1 | 1/2007 | Utas |
| 2007/0160802 A1 | 7/2007 | Rozant |
| 2007/0184275 A1 | 8/2007 | Gilman |
| 2007/0287800 A1 | 12/2007 | Acquarulo |
| 2012/0121919 A1 | 5/2012 | Nielsen |
| 2014/0180261 A1* | 6/2014 | Nyman ................. A61L 29/085 604/544 |
| 2014/0193474 A1 | 7/2014 | Babcock et al. |
| 2014/0363562 A1 | 12/2014 | Nielsen et al. |

FOREIGN PATENT DOCUMENTS

| | | |
|---|---|---|
| WO | 1998/58988 A1 | 12/1998 |
| WO | 2007/011287 A1 | 1/2007 |

OTHER PUBLICATIONS

International Search Report and Written Opinion dated May 24, 2017 for International Application No. PCTUS2017/018073.

* cited by examiner

*Primary Examiner* — Ruiyun Zhang
(74) *Attorney, Agent, or Firm* — Cook Alex Ltd.

(57) ABSTRACT

A urinary catheter having an insertable shaft formed from a blend of an ethylene and/or propylene based polymer and water swellable material. The catheter having a hydrophilic coating disposed on the outer surface of the insertable catheter shaft.

15 Claims, 1 Drawing Sheet

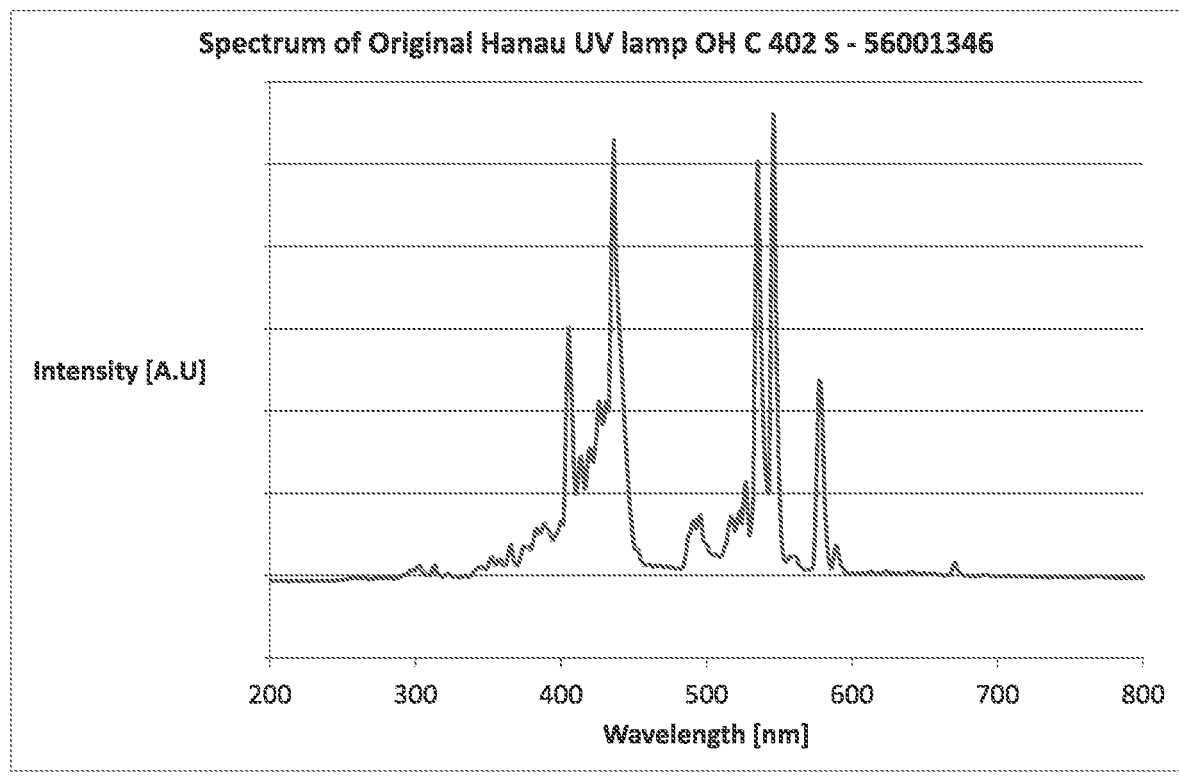
Spectrum of the UV lights utilised to cure the coating.

MEDICAL DEVICE WITH HYDROPHILIC COATING

RELATED APPLICATION

The present application is a continuation of U.S. Nonprovisional application Ser. No. 16/077,129, filed Aug. 10, 2018, which is the U.S. National Stage of PCT International Application No. PCT/US2017/018073, filed Feb. 16, 2017, which claims the benefit and priority of U.S. Provisional Application No. 62/298,728, filed Feb. 23, 2016, all of which are hereby incorporated herein by reference.

TECHNICAL FIELD

The present disclosure relates to medical devices which have a substrate including a hydrophilic coating thereon. More particularly, the present disclosure relates to medical devices for insertion into a body and, even more particularly, medical devices for insertion into lumens or passageways of the body, e.g., urinary catheters and endoscopes. The present disclosure also relates to methods of using and making such medical devices.

BACKGROUND

In the medical field, and in other fields as well, the surface of a device may be coated with a hydrophilic coating that becomes lubricious upon contact with water to ease insertion of the device into the body. Such lubricious hydrophilic coatings may be disposed on urinary catheters, vascular catheter, catheter guide wires, and other medical devices that are meant to be inserted into the body. The lubricious nature of such materials allows the insertion (and subsequent removal) of a catheter or other medical device to be accomplished with minimum resistance, thereby reducing discomfort and possible injury.

While the use of lubricious hydrophilic coatings on medical devices is becoming more common, it remains difficult to prepare a lubricious hydrophilic coating that securely attaches to the substrate surface. Secure attachment of the lubricious coating to the substrate surface is generally desirable and particularly useful in the medical field, where secure attachment of the coating is often an important requirement.

In many instances, securing the hydrophilic coating to a substrate surface includes the use of primer layer or tie layer that has good attachment to both the substrate surface and the hydrophilic layer. When a primer layer is employed, the primer layer is disposed or coated onto the surface of the medical device, after which the top hydrophilic coating is disposed on the primer layer. The primer layer attaches to both the substrate surface and the hydrophilic layer to securely attach the hydrophilic layer to the substrate. While the use of a primer layer may provide sufficient attachment of the hydrophilic coating, such use may be undesirable because it requires the use of an extra coating layer and additional steps and time in the preparation and manufacture of the medical device.

Therefore, there is a need for medical devices that have a hydrophilic coating securely anchored directly to the surface of the substrate of the medical device without the use of a primer layer.

BRIEF SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a urinary catheter includes a catheter tube wherein at least a portion of the catheter tube is made from a blend of an ethylene and/or propylene based polymer and a water-swellable polymer. The catheter also includes a hydrophilic coating disposed on at least a portion of an outer surface of the catheter tube. The ethylene and/or propylene based polymer may have a density less than or equal than 0.95 g/cm$^3$. Additionally, the outer surface of the catheter tube may have a surface energy of at least about 30 mN/m.

In another aspect, a urinary catheter includes a catheter tube wherein at least a portion of the catheter tube is made from a blend of an ethylene and/or propylene based polymer and a water-swellable material.

In yet another aspect, a method of making a urinary catheter that includes the step of blending an ethylene and/or propylene based polymer with a water swellable material to form a blend. The blend is formed into a urinary catheter tube having an outer surface and a hydrophilic coating is disposed on the outer surface.

BRIEF DESCRIPTION OF DRAWINGS

FIG. 1 is a graph representing the spectrum of the light utilized to cure and dry the coating in the Examples.

DETAILED DESCRIPTION

While the subject matter of the present disclosure is susceptible to embodiments in various forms, there will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

The present disclosure is directed to lubricious medical devices that include a lubricious hydrophilic coating disposed on the outer surface of the substrate of the medical device to enhance the lubricity of the medical device so as to ease the insertion of the device into the body and reduce discomfort during insertion and remove of the device. The medical devices include a substrate that is made from a blend or mixture that includes an ethylene and/or propylene based polymer and one or more water swellable materials, such as water swellable polymers. As used herein, the term "polymer" is inclusive of homopolymers and copolymers. The blend also may include other compositions and/or additives, such as compatibilizers/stabilizers.

The lubricious hydrophilic coating may be disposed directly on and adhered directly to the outer surface of the substrate. The surface of the substrate may be a non-treated surface in that the surface is not pre-cleaned with solvents and/or pretreated with plasma, corona, etc. prior to forming the hydrophilic coating on the surface of the substrate. The blend of ethylene and/or propylene based polymer and a water swellable material provides a substrate surface to which the lubricious hydrophilic coating is sufficiently secured without the need for a primer layer. In one embodiment, the lubricious hydrophilic coating is secured directly to the substrate surface without any covalent bonding between the coating and the substrate surface and/or without the formation of an interpenetrating polymer network between the coating and the substrate surface. In one embodiment, the substrate surface includes polar groups that are capable of bonding with the hydrophilic coating to form sufficient attachment without covalent bonding and/or an interpenetrating polymer network.

Although pre-treatments and/or a primer layer may not be necessary, in other embodiments, the lubricious hydrophilic coating may be applied and adhered to the outer surface of the substrate that has been pretreated and/or with the use of a primer layer.

The medical devices of the present disclosure may be, for example, those that are configured for insertion into a lumen of a human body, such as the urethra, fallopian tubes, nasal passages or esophagus. Such medical devices may include, but are not limited to, urinary catheters and endoscopes. While the subject matter disclosed herein may be described relative to urinary catheters, the subject matter is not limited to such and such subject matter may apply to other suitable medical devices as well.

Urinary catheters typically include a catheter tube or shaft that has an insertable portion that is inserted through the urethra and into the bladder to drain urine therefrom. The catheter tube may include a proximal end portion which is inserted through into and through the urethra and into the bladder. The proximal end portion may have drainage eyes or holes that allow urine to drain out of the bladder and into and through the catheter tube. The catheter tube also includes a distal end portion that may have a drainage element, such as a funnel, associated therewith to drain the urine into a collection container, such as a toilet or waste collection bag.

In one embodiment of a urinary catheter of the present disclosure, the catheter includes a catheter tube, i.e. a substrate, having an outer surface that is at least partially coated with a lubricious hydrophilic coating. The lubricous hydrophilic coating is in direct contact with the outer surface of the catheter tube without the use of a primer layer between the outer surface of the catheter tube and the lubricous hydrophilic coating. Preferably, the substrate surface of the catheter tube includes polar groups that are capable of bonding with the hydrophilic coating to sufficiently attach the coating to the surface of the catheter tube without covalent bonding and/or an interpenetrating polymer network between the coating and the surface of the catheter tube.

The catheter tube may be made from a polymer blend or mixture that includes an ethylene and/or propylene based polymer and a water-swellable material, such as a water swellable polymer. In one embodiment, the ethylene and/or propylene based polymer has a density of less than or equal to 0.95 g/cm$^3$. The reduced density of the polymer may be due to, for example, a hindering of crystalline structure. Such polymers may include, for example, ethylene based olefin plastomers, such as copolymers of ethylene and an alpha-olefin which hinders crystalline structure. The alpha-olefin may be, for example, 1-butene, 1-hexene or 1-octene. In one embodiment, the polymer may be an ethylene based 1-octene plastomer. One exemplary commercially available polymer having a density less than or equal to 0.95 g/cm$^3$ is Queo™ 8210, supplied by *Borealis*, Vienna Austria. Other commercially available products may include, for example, Mitsui Chemicals Tafmer DF840, Dow's Versify elastomers and plastomers such as Versify 2300 and Versify 3300, Dow's Attane 4404G, Ateva 2820A, Madalist MD575, Medalist MD585 and/or other styrene ethylene butylene styrene (SEBS) thermoplastic elastomers.

As used herein the term "water swellable material" refers to materials that swell in the presence of water. Generally, any water swellable materials or mixtures thereof could be used in the blend. Preferably, the water swellable material contained in the blend is a material that swells in water but will not swell to the point of destroying the dimensions and/or functionality of the medical device. In other words, the material will swell while maintaining the dimensional stability and/or functionality of the medical device. In one embodiment, the water swellable materials are those that swell in water but do not swell more than 50% of their original non-swollen weight when in contact with water at 25° C. for a period of 1 hour. Suitable water-swellable materials include but are not limited to water swellable ethylene based copolymers, water swellable polyimide-based copolymers, water swellable polyester-based copolymers, water swellable polyether based copolymers, water swellable urethane-based copolymers, and mixtures thereof. Any of a variety of thermoplastic polymers, thermoplastic elastomers, and/or thermoplastic alloys, which are capable of swelling in the presence of water, may be used. Preferably, the water swellable materials are extrusion grade. Water swellable polymers may include, for example, ethylene vinyl alcohol copolymer, polyvinyl alcohol, polyether block amide and thermoplastic polyurethanes. For example, the water swellable polymer may be ethylene vinyl alcohol. The ethylene vinyl alcohol may have between about 20 wt % and about 50 wt % ethylene and about 50 wt % to about 80 wt % vinyl alcohol.

In one embodiment, the ethylene and/or propylene based polymer may be between about 5 wt % and about 95 wt % of the blend and the water swellable material may be about 95 wt % and about 5 wt % of the blend. Preferably, the ethylene and/or propylene based polymer may be between about 80 wt % and about 95 wt % of the blend and the water swellable material may be about 20 wt % and about 5 wt % of the blend. More preferably, the ethylene and/or propylene based polymer may be about 90 wt % of the blend and the water swellable material may be about 10 wt % of the blend.

Optionally, the blend may also include a compatibilizer that may promote interfacial adhesion and stabilization between the ethylene and/or propylene based polymer and water swellable polymer. In one embodiment, the compatibilizer may be an acid modified polyolefin, such as an acrylic acid modified polyolefin. For example the blend may include between about 5 wt % and 20 wt % of the compatibilizer. In one embodiment, the blend may include ethylene and/or propylene based polymer in an amount between about 70 wt % and about 90 wt % of the blend, a water swellable polymer or copolymer in an amount of between about 20 wt % and 5 wt % of the blend, and a compatibilizer in an amount of between about 10 wt % and about 5 wt %.

In one embodiment, a substrate (e.g., a catheter or other medical device) is formed from an ethylene and/or propylene based polymer and water swellable polymer blends wherein the surface of the substrate includes polar groups capable of bonding to a hydrophilic coating. Such polar groups include for example, hydroxyl groups, carboxyl groups, ether groups and amide groups. Preferably, the surface of the substrate is capable of forming polar bonds with the hydrophilic coating such that the coating is sufficiently attached to the substrate surface without the formation of covalent bonds and/or an interpenetrating polymer network between the substrate surface and the hydrophilic coating. In one embodiment, the surface energy of the substrate surface is at least 30 mN/m. In one example, at least a portion of a substrate, such as a catheter tube or other medical device, is made from a blend of an ethylene and/or propylene based polymer having a density less than or equal to 0.95 g/cm$^3$ and a water-swellable polymer. The substrate also has a surface that has a surface energy of at least 30 mN/m and includes polar groups capable of bonding to a hydrophilic coating, and preferably capable of forming sufficient attachment of the coating to the substrate surface without the formation of covalent bonds and/or an interpenetrating polymer network.

Turning to the hydrophilic coating disposed on the outer surface of the catheter tube. The hydrophilic coating includes a hydrophilic polymer capable of providing hydrophilicity to the coating and lubriciousness when the coating is hydrated. The polymer may be synthetic or bio-derived and can be blends or copolymers of both. Suitable hydrophilic polymers include but are not limited to poly(lactams), for example polyvinylpyrollidone (PVP), polyurethanes, homo- and copolymers of acrylic and methacrylic acid, polyvinyl alcohol, polyvinylethers, maleic anhydride based copolymers, polyesters, vinylamines, polyethyleneimines, polyethyleneoxides, poly(carboxylic acids), polyamides, polyanhydrides, polyphosphazenes, cellulosics, for example methyl cellulose, carboxymethyl cellulose, hydroxymethyl cellulose, and hydroxypropylcellulose, heparin, dextran, polysacharrides, for example chitosan, hyaluronic acid, alginates, gelatin, and chitin, polyesters, for example polylactides, polyglycolides, and polycaprolactones, polypeptides, for example collagen and fibrins.

In one embodiment, the hydrophilic polymer coating may include poly(lactams), for example polyvinylpyrollidone (PVP), polyurethanes, homo- and copolymers of acrylic and methacrylic acid, polyvinyl alcohol, polyvinylethers, maleic anhydride based copolymers, polyesters, vinylamines, polyethyleneimines or polyethyleneoxides. Preferably, the hydrophilic polymer coating comprises polyvinylpyrrolidone (PVP).

The hydrophilic polymer may have weight average molecular weight (Mw) from about 20,000 to about 1,300,000, and preferably in the range of about 300,000 to about 400,000. Additionally, the amount of hydrophilic polymer in the coating may be between about 90 wt % and about 98 wt % of the total dry weight of the dry coating.

The hydrophilic coating may be applied to the catheter surface in the form of a solution or a dispersion including a liquid medium (hydrophilic coating composition/formulation), which is dried or cured after the liquid medium has been deposited on the catheter. For example, the hydrophilic coating formulation wets the surface of catheter and then is exposed to UV light to cure the formulation and form the coating. The liquid medium may be any suitable medium that allows application or wetting of the hydrophilic coating formulation on the surface of the substrate. Such liquid media may include water, alcohols, for example methanol, ethanol, propanol, butanol and aqueous mixtures thereof or acetone, methyl ethyl ketone, tetrahydrofuran, dichloromethane, toluene, and aqueous mixtures or emulsions thereof.

The hydrophilic coating may additionally include various additives such as dispersing and stabilizing agents (surfactants or emulsifiers), antioxidants, photoinitiator and curing agents, such as UV curing agents.

For example, the hydrophilic coating formulation may include, in dry weight percentages, about 95 wt % to about 98 wt % a hydrophilic polymer and about 2 wt % to about 5 wt % photoinitiator and/or other additives. In the topcoat solution, the total solid contents may be about 3 wt % to about 8 wt % of the solution.

In one embodiment of making a catheter, the ethylene and/or propylene based polymer and water swellable materials, and optionally additives, are compounded. The blend may be compounded, for example, in a twin screw extruder. The compounding may take place at temperatures in the range of about 180° C.-200° C. The compounded blend may then be cooled from the melt in a water bath at room temperature. The cooled blend is then pelletized. The pelletized blend may then be dried. For example, the drying may be for 4-6 hours at 35° C. The pelletized blend may be used to form catheters by any suitable process, such as by injection molding or extrusion.

The hydrophilic coating may then be applied to the catheter. The hydrophilic coating may be applied in suitable manner. For example, the hydrophilic coating may be applied by dip coating, brushing or spraying. After the coating is applied, the coating is cured by, for example, UV curing.

EXAMPLES

Materials

Unless otherwise stated, the following materials were used in the Examples described below.

Ethylene based polymer (EBP) supplied by *Borealis*, Vienna Austria, under the name QUEO™ 8210.

Polyether block amide (PEBAX) supplied by Arkema, Colombes France, under the name PEBAX MV1074.

Polyvinyl alcohol (PVOH) supplied by Kuraray, Tokyo Japan, under the name Mowiflex TC 661.

Polyvinylpyrrolidone (PVP) 90K supplied by Fluka.

Ethylene vinyl alcohol (EVAL) supplied by EVAL Europe, under the name EVAL.

Acid modified polyolefin (Tafmer) supplied by Mitsui Chemicals, Dusseldorf Germany, under the name Tafmer MA9015.

Thermoplastic polyurethane (TPU) supplied by Lubrizol Corp., Belper England, under the name Tecophilic HP93A100.

Benzophenone supplied by Sigma Aldrich.

Alpha-hydroxy ketone supplied by Lamberti, Italy, under the name Esacure One.

Example 1

Substrates A-C were made from polymer blends A-C which include EBP and PEBAX in the ratios listed in Table 1.

TABLE 1

| Substrate | Blend |
| --- | --- |
| A | Blend A - 90 wt % EBP: 10 wt % PEBAX |
| B | Blend B - 80 wt % EBP: 20 wt % PEBAX |
| C | Blend C - 70 wt % EBP: 30 wt % PEBAX |

Blends A-C were made by compounding EBP and PEBAX, in the above respective ratios, in a twin screw extruder to form the polymer blend. The EBP and PEBAX were compounded at temperatures in the range of about 180° C.-200° C. The compounded polymers where cooled from the melt in a water bath at room temperature and pelletized. The pelletized blends were dried for 4-6 hours at 35° C. An injection molding machine was used to form each of the respective pelletized blends into dog bone shaped substrates A-C.

An EBP only substrate, substrate D, was made by injection molding pelletized EBP into a dog bone shape.

The tensile mechanical properties of each of the substrates A-D were characterized using an Instron testing machine. The average modulus for each substrate was calculated from the testing of five samples and is listed in Table 2 below.

TABLE 2

| Substrate | Modulus [MPa] |
| --- | --- |
| A | 9.8 |
| B | 17.2 |
| C | 22.8 |
| D | 9.1 |

Water uptake measurements were obtained by placing substrates A-C in water at room temperature. Weight measurements of the substrates where taken at the time intervals listed below in Table 3. The average percent of weight gain as a function of time was calculated from testing five samples of each substrate and is reported in Table 3.

TABLE 3

| | Days | | | | |
| --- | --- | --- | --- | --- | --- |
| Substrate | 0 Water uptake % | 6 Water uptake % | 13 Water uptake % | 21 Water uptake % | 72 Water uptake % |
| A | 0 | 0.91 | 1.29 | 1.58 | 1.72 |
| B | 0 | 2.57 | 3.51 | 4.18 | 4.52 |
| C | 0 | 4.96 | 6.59 | 7.67 | 8.25 |

The tensile mechanical properties of substrates A-D were measured after the substrate was immersed in water for a period of 6 days and gamma irradiated with a dose in the range between about 25 kGy and about 40 kGy. The average of the tensile modulus of the wet irradiated substrates was calculated from five samples of each substrate and is reported in Table 4.

TABLE 4

| Substrate | Wet Irradiated Modulus [MPa] |
| --- | --- |
| A | 3.1 |
| B | 6.6 |
| C | 10.4 |
| D | 9.5 |

Example 2

Substrates E-G were made from polymer blends E-G which include EBP and PVOH in the ratios listed in Table 5.

TABLE 5

| Substrate | Blend |
| --- | --- |
| E | Blend E - 90 wt % EBP: 10 wt % PVOH |
| F | Blend F - 20 wt % EBP: 20 wt % PVOH |
| G | Blend G - 70 wt % EBP: 30 wt % PVOH |

Blends E-G were made by compounding EBP and PVOH, in the above respective ratios, in a twin screw extruder to form the polymer blend. The EBP and PVOH were compounded at temperatures in the range of about 180° C.-200° C. The compounded polymers where cooled from the melt in a water bath at room temperature and pelletized. The pelletized blends were dried for 4-6 hours at 35° C. An injection molding machine was used to form each of the respective pelletized blends into dog bone shaped substrate E-G.

The tensile mechanical properties of each of the substrates E-G were characterized using an Instron testing machine. The average modulus for each substrate was calculated from the testing of five samples and is listed in Table 6 below.

TABLE 6

| Substrate | Modulus [MPa] |
| --- | --- |
| E | 14.3 |
| F | 25.5 |
| G | 43.3 |

Water uptake measurements were obtained by placing substrates E-G in water at room temperature. Weight measurements of the substrates where taken at the time intervals listed below in Table 7. The average percent of weight gain as a function of time was calculated from testing five samples of each substrate and is reported in Table 7.

TABLE 7

| | Days | | | | |
| --- | --- | --- | --- | --- | --- |
| Substrate | 0 Water uptake % | 6 Water uptake % | 13 Water uptake % | 21 Water uptake % | 72 Water uptake % |
| E | 0 | 1.88 | 2.87 | 3.62 | 4.00 |
| F | 0 | 3.58 | 5.33 | 6.66 | 7.39 |
| G | 0 | 6.65 | 9.78 | 12.35 | 13.88 |

The tensile mechanical properties of substrates E-G were measured after the substrate was immersed in water for a period of 6 days and gamma irradiated with a dose in the range between about 25 kGy and about 40 kGy. The average of the tensile modulus of the wet irradiated substrates was calculated from five samples of each substrate and is reported in Table 8.

TABLE 8

| Substrate | Wet Irradiated Modulus [MPa] |
| --- | --- |
| E | 7.0 |
| F | 10.8 |
| G | 11.5 |

Example 3

Each of the pelletized blends A-C from Example 1 and E-G from Example 2 above were injection molded to form tubular urinary catheters A-C and E-G, respectively. Each of the catheters had a length of 95 mm and drainage eyes in the proximal end portion of the catheter. A hydrophilic coating was applied directly to the outer untreated surface (no washing with solvent or treating with plasma, corona etc.) of each of the catheters by dip coating. The hydrophilic coating included about 5 wt % polyvinylpyrrolidone and about 0.1 wt % benzophenone in the coating solution. The polyvinylpyrrolidone and benzophenone were dissolved in a solvent including a mixture of water/isopropyl alcohol. The ratio of water to isopropyl alcohol in the solvent was 30:70, and the solvent was at about 94.9 wt % and the dissolved polyvinylpyrrolidone and benzophenone were at about 5.1 wt %. To coat each of the catheters, the catheters were immersed in the coating for 90 seconds and then retracted from the coating at 0.9 cm/s. The catheters with the coating thereon were exposed to electromagnetic radiation for 10 minutes to deliver a dose sufficient to cross-link the coating and remove the solvent. The spectrum of the electromagnetic radiation utilized to cross-link the coating is shown in FIG. 1 and was measured in the range 200-800 nm with a Hamamatsu UV/vis mini spectrometer model C10082MD.

Initial and abraded coefficient of friction (CoF) were measured for each of the coated catheters A-C and E-G. To measure both the initial and abraded CoF, CoF was measured using a Harland Friction Tester Model FTS5500. During the CoF measurement, the proximal end portion of the catheter is cut (13 mm from the tip end of the catheter) and a mandrel was inserted into the remaining section of the coated catheter of the coated catheter tube. The tube was then clamped between two pieces of silicone rubber at 100 g load wherein the silicone rubber had a Shore hardness of 60 A. The tube with the mandrel inserted therein was pulled through the two pieces of silicone rubber at a speed of 10 mm/s. The force required to pull about 40 mm of the tube through the two pieces of silicone rubber was measured and recorded using a universal tensile tester equipped with a 200 N load cell. The CoF value was calculated from the ratio of recorded to applied loads (i.e., the recorded load divided by 2 times the applied load or 200 g) when steady state was reached.

To measure the initial CoF, the coated catheters A-C and E-G were immersed in water for 30 seconds prior to conducting CoF testing in the above-identified manner. For the abraded CoF measurements, catheters A-C and E-G were placed in a water bath and abraded 50 times by passing the catheter tubes back and forth 25 times through 4.14 mm diameter hole in a 1 mm thick silicone pad with Shore hardness of 60 A. The abrading took place while the catheter was immersed in the water bath. This test is designed to remove any portions of the coating that are not well adhered to the catheter. The CoF of the abraded catheters were measured in the above-described manner.

Table 9 shows a summary of the CoF results for catheters A-C and E-F. CoF testing was not performed on catheter G because the surfaces of the molded parts were irregular and not coated. In cases A-C and E-F, the abraded CoF is low, indicating the coating is well anchored onto the catheter substrate without the need of a Primer coating.

TABLE 9

| Catheter | Initial CoF | Abraded CoF |
| --- | --- | --- |
| A | 0.0191 | 0.0224 |
| B | 0.0412 | 0.0288 |
| C | 0.0310 | 0.0279 |
| E | 0.0225 | 0.0231 |
| F | 0.0269 | 0.0253 |
| G | N/A | N/A |

Example 4

Tubing samples H-N were made from the blends shown in Table 10 below.

TABLE 10

| Tubing Sample | Blends |
| --- | --- |
| H | Blend H - 98 wt % EBP: 2 wt % PVOH |
| I | Blend I - 90 wt % EBP: 10 wt % PVOH |
| J | Blend J - 80 wt % EBP: 20 wt % EVAL |
| K | Blend K - 90 wt % EBP: 10 wt % EVAL |
| L | Blend L - 90 wt % EBP: 10 wt % TPU |
| M | Blend M - 85 wt % EBP: 10 wt % PEBAX: 5 wt % Tafmer |
| N | Blend N - 90 wt % EBP: 10 wt % PEBAX |

Each of the blends H-N was made by compounding the above listed respective components for each blend in a twin screw extruder to the polymer blends. The components were compound at temperatures in the range 180° C.-200° C. using a twin screw extruder. Each of the compounded blends was cooled from the melt in a water bath at room temperature and pelletized into polymer chips. The pelletized blends were dried for 4-6 hours at 35° C. prior to tube extrusion. Each of the pelletized blends was then extruded into tubes. Each of the tubes H-N had inner and outer diameters of 3.1+/−0.1 mm and 4.6+/−0.13 mm, respectively.

Surface Energy Measurements

Surface energy measurements were carried out on each of tubes H-N. The measurements were carried out with Arcotest test pens. Eight pens were used in the ranged from 30-44 mN/m wherein the pens differed in 2 mN/m increments (30, 32, 34, etc.). The accuracy of the pens were +/−1 mN/m. The surface energy measurements were taken by marking a piece of the tubing with the pen having an ink with surface tension of 30 mN/m. The ink mark was then observed to determine if the pen's ink wets the surface of the tube or if it de-wets forming droplets of liquid onto the surface. If the ink wetted the surface, it was concluded that the surface energy of the tube is greater than or equal than 30 mN/m. If the ink de-wetted the surface, it was concluded the surface energy of the tube is less than 30 mN/m. If the ink wetted the surface, then the next ink having surface tension of 32 mN/m was utilized to evaluate the surface energy of the tube. This procedure was continued until the surface energy of the tube is obtained.

TABLE 11

| Tubing Sample | Surface Energy [mN/m] |
| --- | --- |
| H | <30 |
| I | 30 |
| J | 30 |
| K | 30 |
| L | 30 |
| M | 30 |
| N | <30 |

Hydrophilic Coating

Each type of tubing sample H-N was coated with a hydrophilic coating without using a primer coating/layer and without pre-treating the surface of the tubing (without pre-treating with a solvent, plasma, corona, etc.). The hydrophilic coating was applied directly to the surfaces of the catheters by dip coating. The hydrophilic coating included about 5% wt % polyvinylpyrrolidone and about 0.1 wt % benzophenone or about 0.1 wt % Esacure One. The polyvinylpyrrolidone and benzophenone or Esacure One were dissolved in a solvent including a mixture of water/isopropyl alcohol. The ratio of water to isopropyl alcohol in the solvent was 30 wt % water to 70 wt % isopropyl alcohol, and the solvent was at about 94.9 wt % and the dissolved polyvinylpyrrolidone and benzophenone or Esacure were at about 5.1 wt %. To coat each of the tubes, the tubes were immersed in the coating for 90 seconds and then retracted from the coating at 0.9 cm/s. The tubes with the coating thereon were exposed to electromagnetic radiation for 10 minutes to deliver the dose required to cross-link the coating and remove the solvent. The spectrum of the electromagnetic radiation utilized to cross-link the coating is shown in FIG. 1 and was measured in the range 200-800 nm with a Hamamatsu UV/vis mini spectrometer model C10082MD.

Initial, abraded and dry-out coefficients of friction (CoF) were measured for each of the coated tubes H-N. A Harland Friction Tester Model FTS5500 was used to measure both the initial and abraded CoF. The procedure for measuring CoF includes inserting a mandrel into a 127 mm section of the coated tubing. The tubing was then clamped between two pieces of silicone rubber at 100 g load wherein the silicone rubber had a Shore hardness of 60 A. The tubing with the mandrel inserted therein was pulled through the two pieces of silicone rubber at a speed of 10 mm/s. The force required to pull about 80 mm of the coated tubing through the two pieces of silicone rubber was measured and recorded using a universal tensile tester equipped with a 200 N load cell. The CoF value was calculated from the ratio of recorded to applied loads (i.e., the recorded load divided by 2 times the applied load or 200 g) when steady state was reached.

For the initial CoF measurement, the coated tubings were immersed in water for 30 seconds prior to CoF testing. For the abraded CoF measurements, the coated tubings were placed in a water bath and abraded 50 times by passing the catheter tubes 25 times back and forth through 4.14 mm diameter hole in a 1 mm thick silicone pad with Shore hardness of 60 A. The abrading took place while the catheter was immersed in the water bath. This test is designed to remove any portions of the coating that are not well adhered to the catheter. Shortly after abrasion, the CoFs of the abraded catheters were measured.

For the dry-out CoF measurement, the each tubing was hydrated in water for 30 seconds and then placed in a controlled atmosphere with a constant relative humidity of 50% RH and a constant temperature of 23° C. for 10 minutes prior to measuring the CoF.

Table 12 shows a summary of the CoF results for tubings H-N and the type of photoinitiator that was used in the coating.

TABLE 12

| Tubing Sample | Initial CoF | Abraded CoF | 10 Min. Dry-out CoF | Photoinitiator |
|---|---|---|---|---|
| H | 0.012 | 0.072 | 0.021 | Esacure One |
| I | 0.032 | 0.061 | 0.043 | Benzophenone |
| J | 0.016 | 0.026 | 0.023 | Esacure One |
| K | 0.014 | 0.014 | 0.036 | Esacure One |
| L | 0.017 | 0.014 | 0.026 | Esacure One |
| M | 0.030 | 0.030 | 0.044 | Benzophenone |
| N | 0.028 | 0.029 | 0.046 | Benzophenone |

Swelling Measurements

A sample of each of the uncoated tubing J-N were weighted in a microbalance and then immersed in a bath of water at 70° C. for 24 hours. The tubings were then removed from the bath of water and weight. For each tubing sample, the initial weight of the tubing and the weight after immersion were compared to determine the percentage of water uptake, the results of which are reported in Table 13 of the were measured after 24 hours of immersion in water.

TABLE 13

| Tubing Sample | Water Uptake [%] |
|---|---|
| J | 1.05 |
| K | 0.46 |
| L | 3.26 |
| M | 2.38 |
| N | 2.15 |

Example 5

The below hydrophilic coating was formed on tubing Samples M and N. The hydrophilic coatings were applied directed to the surface of the tubing without using a primer coating/layer and without pre-treating the surface of the tubing. The hydrophilic coating was applied directly to the surfaces of the catheters by dip coating.

The hydrophilic coating composition/formulation was prepared with the components as shown in the table below.

TABLE 14

| Component | Amount (w/w) |
|---|---|
| Ethanol (absolute) (Lennox) | 78.99% (w/w) |
| De-ionized water (Lennox) | 14.00% (w/w) |
| PVP K90 (Ashland) | 5.95% (w/w) |
| BHT-A (Sigma Aldrich) | 0.01% (w/w) |
| PEG400DA (SR344, Sartomer, inhibitor removed) | 0.30% (w/w) |
| Glycerol | 0.74% (w/w) |
| Benzophenone | 0.01% (w/w) |

The hydrophilic coating composition was prepared by adding PVP to the ethanol and water and mixing until dissolved. The remaining components (glycerol, PEG400DA, BHT-A, and benzophenone) were then added and allowed to fully dissolve under stirring.

To form the hydrophilic coating on the outer surfaces of the catheters, the catheters were then immersed in the hydrophilic coating composition for 90 seconds and withdrawn at a rate of 0.9 cm/sec. The hydrophilic coating composition was then UV cured and dried under UV lamps for 6.4 minutes to form the hydrophilic coating on the catheter.

The initial, abraded and 10-minute dry-out CoFs were measured in the same manner as described about. The results of which are shown in Table 15 below.

TABLE 15

| Sample Set | Initial CoF Avg. | Abraded CoF Avg. | 10 Min Dry-out Avg. |
|---|---|---|---|
| M | 0.029 | 0.029 | 0.035 |
| N | 0.026 | 0.030 | 0.035 |

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A method of making a urinary catheter comprising:
blending between about 80 wt % and about 95 wt % of a copolymer of ethylene and an alpha-olefin with between about 5 wt % and about 20 wt % of a water-swellable material comprising vinyl alcohol polymer to form a blend;
forming the blend into a urinary catheter tube having an untreated outer surface; and
forming a hydrophilic coating directly on the outer surface.

2. The method of claim 1 wherein forming the blend into a urinary catheter tube comprises extruding or molding the blend into a urinary catheter tube.

3. The method of claim 1 wherein the water-swellable material comprises a polymer or co-polymer selected from the group consisting of ethylene vinyl alcohol copolymer and polyvinyl alcohol polymer.

4. The method of claim 3 wherein the water-swellable material comprises ethylene vinyl alcohol copolymer.

5. The method of claim 4 wherein the ethylene vinyl alcohol copolymer comprises between about 20 wt % and about 50 wt % ethylene and about 50 wt % and about 80 wt % vinyl alcohol.

6. The method of claim 4 wherein blend includes between about 80 wt % and about 95 wt % of the copolymer of ethylene and an alpha-olefin and between about 5 wt % and about 20 wt % ethylene vinyl alcohol copolymer.

7. The method of claim 1 wherein the alpha-olefin is selected from the group consisting 1-butene, 1-hexene and 1-octene.

8. The method of claim 7 wherein the alpha-olefin comprises 1-octene.

9. The method of claim 1 wherein the blending further includes blending a compatibilizer with the copolymer of ethylene and an alpha olefin and water swellable material.

10. The method of claim 9 wherein the compatibilizer is between about 5 wt % and about 20 wt % of the blend.

11. The method of claim 9 wherein the compatibilizer comprises an acid modified polyolefin.

12. The method of claim 1 wherein the hydrophilic coating comprises polyvinylpyrrolidone.

13. The method of claim 1 wherein the copolymer of ethylene and an alpha olefin polymer has a density less than or equal than $0.95 \text{ g/cm}^3$.

14. The method of claim 1, wherein the hydrophilic coating comprises a single layer in direct contact with the outer surface of the catheter tube.

15. The method of claim 1, wherein there is no primer layer between the outer surface of the catheter tube and the hydrophilic coating.

* * * * *